United States Patent [19]

DeLuca et al.

[11] 4,195,027

[45] Mar. 25, 1980

[54] PROCESS FOR PREPARING 1α-HYDROXYLATED COMPOUNDS

[75] Inventors: Hector F. DeLuca; Heinrich K. Schnoes; David E. Hamer; Herbert E. Paaren, all of Madison, Wis.

[73] Assignee: Wisconsin Alumni Research Foundation, Madison, Wis.

[21] Appl. No.: 914,796

[22] Filed: Jun. 12, 1978

Related U.S. Application Data

[63] Continuation-in-part of Ser. No. 869,448, Jan. 16, 1978, abandoned.

[51] Int. Cl.² .............................................. C07J 9/00
[52] U.S. Cl. .................................................. 260/397.2
[58] Field of Search ...................................... 260/397.2

[56] References Cited

U.S. PATENT DOCUMENTS

| 3,929,770 | 12/1975 | Ishikawa et al. | 260/397.2 |
| 3,976,636 | 8/1976 | Salmond | 260/397.2 |

*Primary Examiner*—Elbert L. Roberts
*Attorney, Agent, or Firm*—Howard W. Bremer

[57] ABSTRACT

A method for directly introducing an oxygen function at carbon 1 of the vitamin D molecule or precursors or derivatives thereof which comprises subjecting such molecules to allylic oxidation utilizing selenium dioxide as the oxidizing agent.

65 Claims, No Drawings

PROCESS FOR PREPARING 1α-HYDROXYLATED COMPOUNDS

The invention described herein was made in the course of work under a grant or award from the Department of Health, Education, and Welfare.

This is a continuation-in-part of our copending application Ser. No. 869,448, filed Jan. 16, 1978, now abandoned.

This invention relates to a method for preparing compounds having vitamin D-like activity and to compounds which are key intermediates in such method.

More specifically, this invention relates to a method for preparing compounds having vitamin D-like activity which contain an oxygen function at carbon 1 in the molecule.

Still more specifically, this invention relates to a method for preparing 1α-hydroxylated compounds which are characterized by vitamin D-like activity via a cyclovitamin D intermediate.

It is well known that the D vitamins exhibit certain biological effects, such as stimulation of intestinal calcium absorption, stimulation of bone mineral resorption and the prevention of rickets. It is also well known that such biological activity is dependent upon these vitamins being altered in vivo, i.e. metabolized, to hydroxylated derivatives. For example, current evidence indicates that 1α,25-dihydroxyvitamin $D_3$ is the in vivo active form of vitamin $D_3$ and is the compound responsible for the aforementioned biological effects.

The synthetic 1α-hydroxyvitamin D analogs, such as 1α-hydroxyvitamin $D_3$, and 1α-hydroxyvitamin $D_2$ also exhibit pronounced biological potency and such compounds as well as the natural metabolites show great promise as agents for the treatment of a variety of calcium metabolism and bone disorders, such as osteodystrophy, osteomalacia and osteoporosis.

Since 1α-hydroxylation is an essential element in imparting biological activity to the vitamin D compounds and their derivatives there has been increasing interest in methods for chemically accomplishing such hydroxylation. Except for one suggested method for the total synthesis of 1α-hydroxyvitamin $D_3$ (Lythgoe et al, J. Chem. Soc., Perkin Trans I, p. 2654 (1974)), all syntheses of 1α-hydroxylated vitamin D compounds prior to the conception of the present invention involved the preparation of a 1α-hydroxylated steroid, from which, after conversion to the corresponding 1α-hydroxy-5,7-diene sterol derivative, the desired vitamin D compound is obtained by well known photochemical methods. Thus available syntheses are multistep processes and in most cases are inefficient and laborious.

A new method for introducing a hydroxyl group at the carbon 1 (C-1) position in the vitamin D or vitamin D derivative molecule has now been found which in concept and execution differs radically from existing syntheses. This method, which will be more fully described hereinafter, provides for the direct introduction of an oxygen function at C-1 by allylic oxidation.

In general, the method of this invention comprises preparing 1α-hydroxylated compounds having the formula

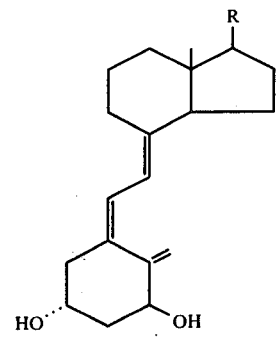

by subjecting compounds (hereinafter referred to by the general term "cyclovitamin D") having the formula

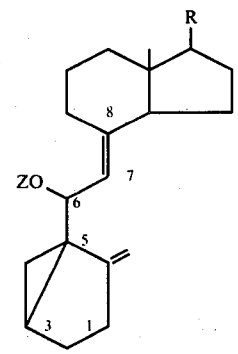

to allylic oxidation, recovering the resulting 1α-hydroxylated cyclovitamin D compound from the allylic oxidation reaction mixture, acylating the recovered compound and recovering the resulting 1α-O-acyl derivative, subjecting said derivative to acid catalyzed solvolysis, recovering the desired 1α-O-acyl vitamin D compound and hydrolyzing (or reducing with hydride reagents) the 1α-O-acylated product to obtain 1α-hydroxyvitamin D compounds.

In the above described process, R in the formulae represents a steroid side chain; most commonly a substituted or unsubstituted, or saturated or unsaturated, or substituted and unsaturated cholesterol side chain group and Z represents hydrogen or a lower alkyl or lower acyl group or aromatic acyl group. Preferably R will be a cholesterol or ergosterol side chain group characterized by the presence of a hydrogen or hydroxy group at what will be the 25-carbon (C-25) position in the desired product molecule.

Wherever herein and in the claims the word "lower" is used as a modifier for alkyl or acyl, it is intended to identify a hydrocarbon chain having from 1 to about 4 carbon atoms and can be either a straight chain or branched chain configuration. An aromatic acyl group is a group such as benzoyl or substituted benzoyl. Also, in the various formulae depicted, a wavy line to any substituent is indicative of that particular substituent being in either the α or β stereoisomeric form.

More specifically, in the practice of the process of this invention, R in the formulae set forth above and those to follow, and in the claims, is preferably a cholesterol side chain group characterized by the formula

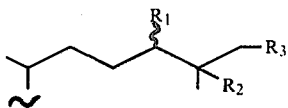

wherein each of $R_1$, $R_2$ and $R_3$ are selected from the group consisting of hydrogen, hydroxy, lower alkyl, substituted lower alkyl, O-lower alkyl, substituted O-lower alkyl, and fluorine. The most preferred side chain group having the above configuration is one where $R_1$ and $R_3$ are hydrogen and $R_2$ is hydroxyl. Other preferred side chain groups are those where $R_1$, $R_2$ and $R_3$ are hydrogen, or where $R_1$ is hydroxyl and $R_2$ and $R_3$ are hydrogen, or where $R_1$ and $R_2$ are hydroxyl and $R_3$ is hydrogen.

Another preferred side chain group represented by R is the ergosterol side chain group characterized by the formula

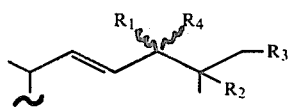

wherein each of $R_1$, $R_2$ and $R_3$ are selected from the group consisting of hydrogen, hydroxyl, lower alkyl, substituted lower alkyl, O-lower alkyl, substituted O-lower alkyl, and fluorine, and $R_4$ is selected from the group consisting of hydrogen and lower alkyl. The most preferred side chain groups having the designated ergosterol side chain configuration are where $R_1$ and $R_3$ are hydrogen, $R_2$ is hydroxyl and $R_4$ is methyl or where $R_1$, $R_2$ and $R_3$ are hydrogen and $R_4$ is methyl and where the stereochemistry of $R_4$ is that of ergosterol.

It is understood that wherever hydroxy groups occur in the side chain group R of the cyclovitamin D starting material, such groups may be acylated, e.g. lower acyl such as acetyl or substituted lower acyl, benzoyl or substituted benzoyl, although such acylation is not required for success of the process.

It is to be noted further that the side chain group R need not be limited to the types enumerated above. The process described in this invention is a general one that is applicable to cyclovitamin D compounds possessing many of the common steroid side chains, e.g. the side chain of pregnenolone, desmosterol, cholenic acid, or homocholenic acid. In addition to the side chain groups defined above, cyclovitamin D compounds wherein the side chain R group is represented for example by the following structures

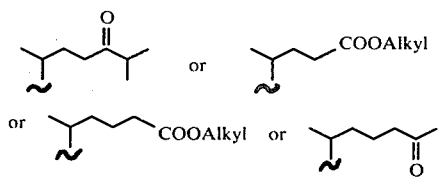

are conveniently prepared and are suitable starting materials for the process of this invention.

The cyclovitamin starting material for the oxidation process is conveniently prepared from a vitamin D compound by a two-step procedure which comprises converting a vitamin D compound carrying a 3β-hydroxy group to the corresponding 3β-tosylate derivative and then solvolyzing this tosylate in a suitable buffered solvent mixture, such as methanol/acetone containing sodium acetate, to yield the cyclovitamin product. Sheves and Mazur (J. Am. Chem. Soc. 97, 6249 (1975)) applied this sequence to vitamin $D_3$, and obtained as major product a cyclovitamin $D_3$ to which they assigned the structure shown below, i.e. 6R-methoxy-3,5-cyclovitamin $D_3$. A minor cyclovitamin formed in this process was identified as the corresponding compound with the methoxy in the 6S configuration.

It has now been found that if the solvolysis reaction is carried out in methanol using $NaHCO_3$ buffer, a better yield of cyclovitamin product than that reported by Sheves and Mazur can be obtained.

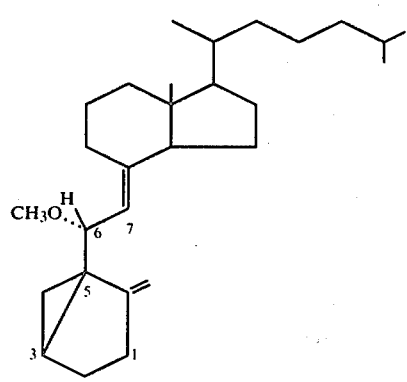

It has now been found that vitamin D compounds carrying other chemically reactive substituents (e.g., side chain hydroxy groups) can be converted efficiently to their cyclovitamin D derivatives. For example, with 25-hydroxyvitamin $D_3$ as the starting material in the above described process 25-hydroxy-6-methoxy-3,5-cyclovitamin $D_3$ is observed. The structure of this compound is shown below, where R represents the 25-hydroxycholesterol side chain. Similarly with 24,25-dihydroxyvitamin $D_3$ as starting material, the above described process leads to 24,25-dihydroxy-6-methoxy-3,5-cyclovitamin $D_3$ represented by the structure shown below where R represents the 24,25-dihydroxycholesterol side chain. With vitamin $D_2$ as the starting material the same process sequence leads to cyclovitamin $D_2$, also represented by the structure below but where R signifies the ergosterol side chain. These cyclovitamin D compounds are new compounds.

In analogy with the results of Sheves and Mazur cited earlier, the 6R-methoxy sterochemistry can be assigned to the major cyclovitamin D product obtained in these reactions, and to the minor constituent (5–10% of the cyclovitamin product mixture the 6S-methoxy configuration. The process of this invention does not require separation of these stereoisomers, it being understood, however, that, if desired, such separation can be accomplished by known methods, and that either C-(6)-epimer can be used although not necessarily with the same process efficiency. For these reasons stereochemical configuration at C-6 of the cyclovitamin D compounds is not designated in the structures of the specification and the claims.

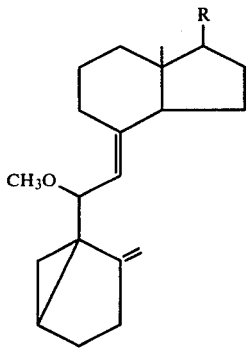

By appropriate choice of suitable reagents or conditions the process of this invention will yield cyclovitamin D analogs illustrated by the following general structure

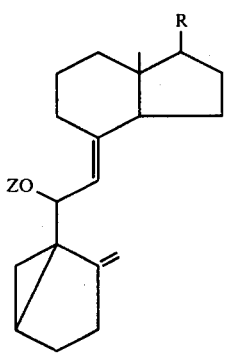

where Z represents hydrogen, alkyl or acyl, and R can represent any of the side chain structure types defined earlier. For example, if ethanol instead of methanol is used in the solvolyzing medium, a cyclovitamin of the structure shown above is obtained, where Z represents ethyl. It is evident that other O-alkylated cyclovitamin D products can be obtained by the use of the appropriate alcohol in the reaction medium.

Similarly a solvolysis reaction medium composed of solvents containing $H_2O$, such as acetone/$H_2O$, or dioxane/$H_2O$, in the presence of an acetate salt or other buffering agent yields the corresponding cyclovitamin D compound of the formula shown above where Z is hydrogen. Sheves and Mazur [Tetrahedron Letters (No. 34) pp. 2987–2990 (1976)] have in fact prepared 6-hydroxycyclovitamin $D_3$, i.e. the compound represented by the structure above where Z is hydrogen and R represents the cholesterol sidechain, by treating vitamin $D_3$ tosylate with aqueous acetone buffered with $KHCO_3$.

It has now been found that a 6-hydroxy cyclovitamin, if desired, can be converted to the corresponding acyl derivative (i.e. Z=acyl, such as acetyl or benzoyl) by acylation using standard conditions (e.g. acetic anhydride/pyridine). The acylated cyclovitamin D of the structure shown above, with Z representing acetyl, can also be obtained as a minor product, when the solvolysis reaction is carried out in a medium of dry methanol containing sodium acetate. The cyclovitamin D compound where Z represents methyl is a preferred starting material for subsequent reactions.

In the process of this invention the allylic oxidation is normally carried out in a suitable solvent, such as, for example, $CH_2Cl_2$, $CHCl_3$, dioxane or tetrahydrofuran, utilizing selenium dioxide as the oxidizing agent. Because of the nature of this oxidation reaction, it is preferable that it be carried out at room temperature or lower temperatures. The oxidation reaction is also most advantageously conducted in the presence of a hydroperoxide, for example, hydrogen peroxide or an alkyl hydroperoxide such as tert-butyl hydroperoxide. The oxidation product, i.e. the 1α-hydroxycyclovitamin D compound, is readily recovered from the reaction mixture by solvent extraction (e.g. ether), and is conveniently further purified by chromatography. Other allylic oxidants can be used if desired, it being understood that with such other oxidants variation in product yield may be encountered and that adjustment of the conditions under which the oxidation reaction is carried out may have to be made, as will be evident to those skilled in the art. The products resulting from allylic oxidation of cyclovitamin D compounds of the structure shown above where Z represents lower alkyl (e.g. methyl) are readily illustrated by the following formula

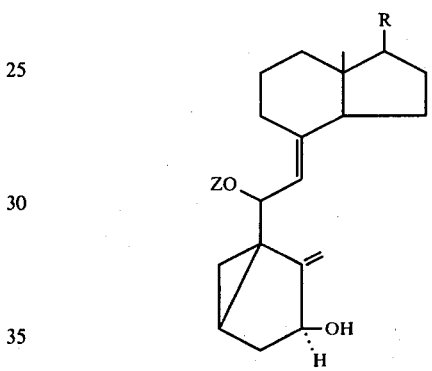

where R represents any of the side chain structures defined earlier, and Z represents lower alkyl (e.g. methyl).

Oxidation of the cyclovitamins by the process of this invention results in the formation of 1-hydroxycyclovitamins possessing the 1α-stereochemistry which is desired, i.e., the stereochemistry of biologically active 1-hydroxylated vitamin D metabolites. The positional and stereochemical selectivity and the remarkable efficiency of the oxidation process is both novel and unexpected and all 1α-hydroxycyclovitamins disclosed are new compounds.

Minor products resulting from selenium dioxide oxidation of cyclovitamin D compounds are 1-oxocyclovitamin D derivatives of the following structure

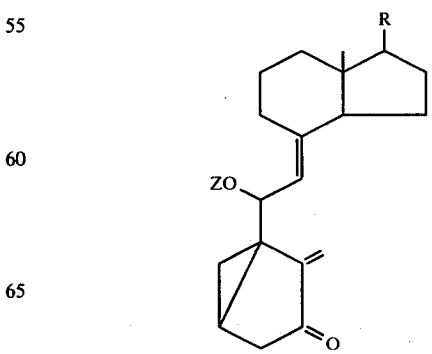

where Z represents lower alkyl and R represents any of the side chain groups defined earlier. These 1-oxocyclovitamin D derivatives are readily reduced by hydride reagents (e.g. LiAlH₄ or NaBH₄ or equivalent reagents) to form predominantly 1α-hydroxycyclovitamin D derivatives of the formula illustrated previously. The facile reduction of 1-oxocyclovitamin D compounds and especially the predominant formation of 1-hydroxycyclovitamin D compounds possessing the 1α-stereochemistry is an unexpected finding, since mechanistic arguments would have predicted approach of the hydride reducing agent from the less hindered side of the 1-oxocyclovitamin D molecule which would lead to the predominant function of the 1β-hydroxycyclovitamin epimer.

The acylation of the recovered 1α-hydroxycyclovitamin D compound is conveniently accomplished by standard methods with well-known acylating reagents, acetic anhydride being one example, in a suitable solvent, e.g. pyridine, and is normally conducted at room temperature over a period of several hours, e.g. overnight. The product of acylation is the corresponding 1α-O-acylcyclovitamin D compound, which is conveniently recovered in a purity sufficient for further reactions by solvent (e.g. ether) extraction from the medium with subsequent evaporation of solvents.

Any primary or secondary hydroxyl groups present in the side chain (R) of the 1α-hydroxycyclovitamin D compound can be expected to be acylated also under these conditions. If complete acylation of tertiary hydroxy groups (e.g. the 25-hydroxy group) is desired, more vigorous acylating conditions are normally required, e.g. elevated temperatures (75°–100° 1 C.). It is advisable in such cases to conduct the reaction under a nitrogen atmosphere to avoid decomposition of labile compounds. Products of such acylations can be illustrated by the formula.

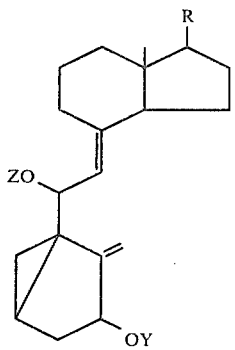

where Y represents a lower acyl group or aromatic acyl group and Z represents lower alkyl and where R can represent any of the steroid side chains defined earlier in this specification, it being understood that secondary or primary hydroxyl groups originally present, will now occur as the corresponding O-acyl substituent, and any tertiary hydroxy group originally present, may be hydroxy or O-acyl depending on the condition chosen.

Conversion of the 1α-O-acyl cyclovitamin to the 1α-O-acyl vitamin D derivative is accomplished by acid-catalyzed solvolysis of the cyclovitamin. Thus, warming 1α-O-acylcyclovitamin D with p-toluenesulfonic acid, in a suitable solvent mixture (e.g. dioxane/H₂O) yields 1α-O-acyl vitamin D compound. Sheves and Mazur used this reaction for the conversion of cyclovitamin D₃ to vitamin D₃ [J. Am. Chem. Soc. 97, 6249 (1975)].

A novel and unexpected surprising finding, not evident from the prior art, was that 1α-O-acyl cyclovitamin D compounds are cleanly converted and in good yield to the corresponding 1α-O-acyl vitamin by acid solvolysis. This result was completed unpredictable since the allylic 1α-oxygen function of an 1α-hydroxycyclovitamin D compound would be expected to be labile to the solvolysis conditions. Indeed, solvolysis of the 1α-hydroxycyclovitamin D is not practical since it leads to a complex product mixture and protection of this hydroxy function as the 1α-O-acyl derivative is required and such protection represents an important element of the present discovery.

It is also important that any tertiary or allylic alcohol functions that may occur in the side chain be protected as the corresponding acylates or other suitable, acid-stable protecting group. The product 1α-O-acyl vitamin D is readily recovered from the solvolysis mixture by solvent extraction and is further purified by chromatography. The solvolysis reaction yields both 1α-O-acyl vitamin D possessing the natural 5,6-cis double bond geometry, and the corresponding 1α-O-acyl vitamin D with a 5,6-trans geometry, in a ratio of ca. 5:1. These products are readily separated by solvent extraction and chromatography to yield in pure form 1α-O-acyl vitamin D product of the general formula illustrated below (as well as, if desired, the corresponding 5,6-transisomer),

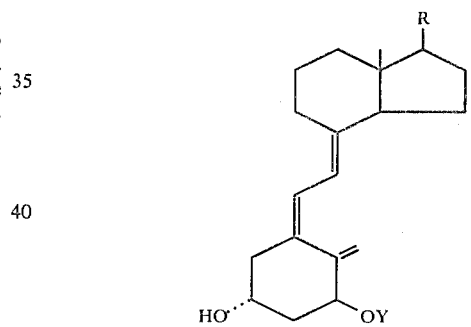

where Y represents a lower acyl group (e.g. acetyl) or aromatic acyl group (e.g. benzoyl) and where R represents any of the steroid side chains defined earlier, it being understood that all hydroxy functions are present as their corresponding O-acyl derivatives.

1α-O-acyl vitamin D derivatives are readily converted to the desired 1α-hydroxyvitamin D compounds by hydrolytic or reductive removal of the acyl protecting group. The specific method chosen would depend on the nature of the compound, in particular also the nature of the side chain R group and its substituents. It is understood for example that hydride reduction would not be employed, if simultaneous reduction of another function susceptible to reduction, e.g. ketone or ester, is to be avoided, or else such functions would be suitably modified prior to reductive removal of acyl groups. Thus, treatment of the acylated compound with a suitable hydride reducing agent (e.g. lithium aluminum hydride) yields the corresponding 1α-hydroxyvitamin D compound. Similarly mild basic hydrolysis (e.g. KOH/MeOH) converts the acylated compound to the desired 1α-hydroxy derivative, it being understood that in cases where the side chain carries sterically hindered (e.g. tertiary) O-acyl groups, more vigorous conditions (elevated temperatures, prolonged reaction times) may be required. The 1α-hydroxyvitamin D compound prepared by either method, is readily recovered in pure form by solvent extraction (e.g. ether) and chromatography and/or crystallization from a suitable solvent.

An alternative and novel method for converting the 1α-O-acyl cyclovitamin D compounds to corresponding vitamin D derivatives consists of acid-catalyzed solvolysis of the cyclovitamin compound in a medium consisting of an organic acid (e.g. acetic acid, formic acid) or of an organic acid with a co-solvent, such as acetone, or dioxane, if required for solubilizing the cyclovitamin. It is a particular advantage of this method that if the side chain group R contains any tertiary hydroxy groups (e.g. the 25-hydroxy group) protection of such functionalities, e.g. as their acyl derivatives, is not necessary. Thus, by way of example, solvolysis of 1α-O-acetoxyvitamin D$_3$ in glacial acetic acid yields 1α-acetoxy vitamin D$_3$ 3β-acetate, as well as some of the corresponding 5,6-trans-compound (product ratio ca. 3:1). These products can be separated by chromatography or the mixture can be hydrolyzed under basic conditions (such as KOH/MeOH) to yield 1α-hydroxyvitamin D$_3$ and the corresponding 1α-hydroxy-5,6-trans-vitamin D$_3$, which can then be separated by chromatography. This method can be applied to any 1α-O-acyl cyclovitamin D compound possessing any of the side chain groups R defined earlier in this specification.

Even more advantageously, solvolysis of 1α-O-acyl cyclovitamins can be carried out in formic acid or formic acid plus a suitable co-solvent such as dioxane. This process leads to the formation of 1α-O-acyl-vitamin D 3β-formate derivatives, illustrated by the following formula:

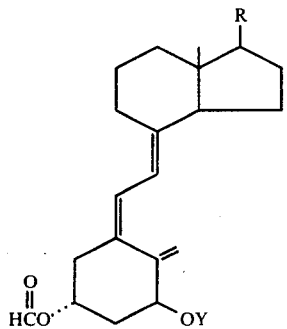

where Y is a lower acyl group (preferably not formyl) or aromatic acyl group and R represents any of the side chain groups defined earlier. Again the corresponding 5,6-trans compound is formed also as a minor product. Since the 3β-O-formyl group is very readily hydrolyzed under conditions where the 1α-O-acyl group is not affected (e.g. by treatment with potassium carbonate in a few minutes, as shown by the specific Examples), the above mixture of 3-O-formyl products are readily converted to 1α-O-acyl vitamin D and its corresponding 5,6-trans isomer. This mixture can be conveniently separated at this stage by chromatographic methods to yield pure 1α-O-acyl vitamin D and the corresponding 5,6-trans-1αO-acyl vitamin D which can now separately be subjected to basic hydrolysis, or to reductive cleavage of the acyl group to yield 1α-hydroxyvitamin D compound, and 5,6-trans-1α-hydroxyvitamin D compound.

Another novel procedure for the conversion of 1α-O-acyl cyclovitamin derivatives to 1α-O-acyl-3β-formyl vitamin D compounds of the formula illustrated above involves use of "crown ether" catalysts. For example, a two-phase system consisting of formic acid and a hydrocarbon (e.g. hexane/benzene) solution of 1α-O-acyl cyclovitamin D containing a suitable crown ether (e.g. 15-crown-5, Aldrich Chemical Co., Milwaukee) and formate ion, converts the 1α-O-acyl cyclovitamin to the 1α-O-acyl-3β-O-formyl vitamin D derivative in good yield. The corresponding 5,6-trans isomer is formed as a minor product and is conveniently separated by chromatography.

A further variation of the methods just described consists of converting a 1α-hydroxycyclovitamin D compound to the corresponding 1α-O-formyl derivative (e.g. by means of acetic-formic anhydride, in pyridine) represented by the following formula

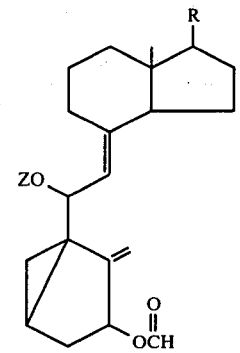

where R represents any of the side chain groups defined herein before and Z represents lower alkyl, and subjecting this intermediate to solvolysis in glacial acetic acid, as previously described, to obtain, 1α-formyloxy vitamin D 3β-acetate and as a minor product the corresponding 5,6-trans isomer. Removal of the formyl group, as described above, yields 1α-hydroxyvitamin D 3-acetate and its 5,6-trans isomer which are conveniently separated at this stage by chromatography and then separately subjected to hydrolysis or reductive cleavage of the acetates to yield a pure 1α-hydroxyvitamin D compound and its 5,6-trans isomer.

The allylic oxidation process of this invention can also be applied to cyclovitamin D compounds bearing 6-hydroxy or 6-O-acyl groups. Thus, cyclovitamin D compounds of the following structure

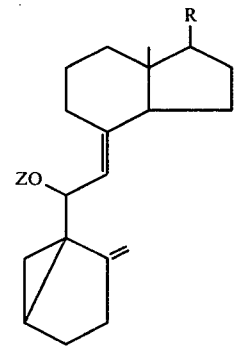

where Z represents hydrogen and R represents any of the sidechain groups defined herein before can be oxidized at carbon 1 by the allylic oxidation process of this invention to yield 1α-hydroxy-6-hydroxycyclovitamin D compounds and 1-oxo-6-hydroxycyclovitamin cyclovitamin D compounds. Under the oxidation conditions previously described, some cycloreversion of the 1α-hydroxy-6-hydroxycyclovitamin D compound to a mixture of 5,6-cis and 5,6-trans-1α-hydroxyvitamin D compounds also occurs. All products are readily recovered from the oxidation mixture by chromatography. The 1α-hydroxy-6-hydroxycycyclovitamin D compounds obtained by allylic oxidation can be acylated (e.g. acetylated) by the standard process described previously and the resulting 1,6-diacyl cyclovitamin D intermediates are readily converted by acid solvolysis as discussed above to 5,6-cis and 5,6-trans-1α-O-acyl vitamin D compounds which are easily separated by chromatography. Hydrolysis (by known methods) of the 1-O-acyl derivatives leads to the desired 1α-hydroxyvitamin D products and their 5,6-trans isomers respectively. The 1-oxo-6-hydroxycyclovitamin D products are readily reduced by hydride reagents the 1α-hydroxycyclovitamin derivatives.

Similarly, cyclovitamin D compounds of the structure shown above where Z represents acyl (e.g. acetyl, benzoyl) and R represents any of the sidechain groups previously defined, can be converted by the sequence of allylic oxidation, acylation, acid solvolysis, and finally hydrolysis of the acyl groups as described for the case of the 6-hydroxy analogues to 1α-hydroxyvitamin D products and their corresponding 5,6-trans isomers.

A further noteworthy and unexpected finding made in the course of this invention is the discovery that 1α-hydroxyvitamin D compounds are readily and efficiently converted to 1α-hydroxycyclovitamin D compounds by solvolysis of the 3β-tosylates (or mesylates) of 1α-hydroxy- or 1α-O-acyl vitamin D derivatives. For example, 1α-acetoxyvitamin $D_3$ 3-tosylate, upon solvolysis using conditions described herein before, e.g., heating in methanol solvent containing $HaHCO_3$, yields 1α-hydroxy-6-methoxy-3,5-cyclovitamin $D_3$. Oxidation of this product (e.g. with $MnO_2$ in $CH_2Cl_2$ solvent) yields the corresponding 1-oxo-6-methoxy-3,5-cyclovitamin $D_3$ analog as described in the specific examples.

In the following examples, which are intended to be illustrative only, the numbers identifying particular products, e.g. 3a for 1α-hydroxycyclovitamin $D_3$, correspond to the numbers designated the various structures for such products as set forth below.

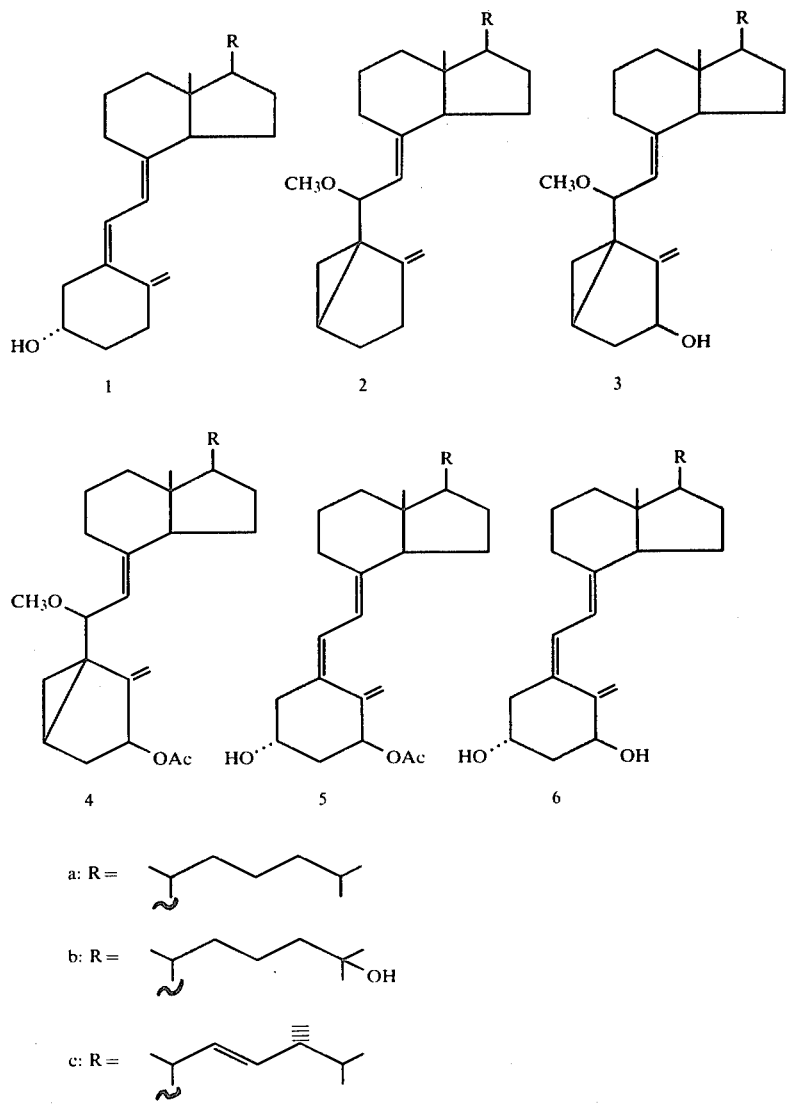

-continued

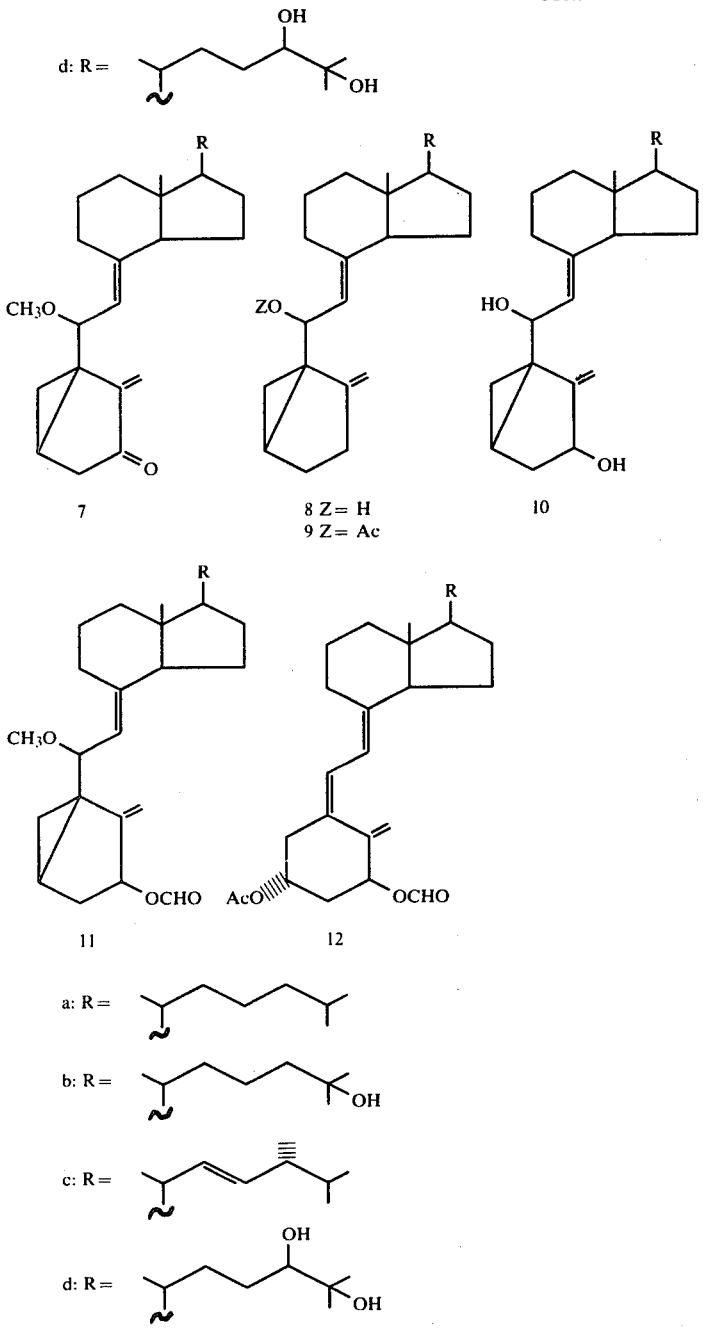

EXAMPLE 1

1α-Hydroxycyclovitamin $D_3$ (3a) and 1-oxo-cyclovitamin $D_3$ (7a)

To a stirred suspension of 1.4 mg ($1.2 \times 10^{-5}$ moles) of $SeO_2$ in 1.0 ml of dry $CH_2Cl_2$ is added 7 μl ($5.1 \times 10^{-5}$ moles) of a 70% solution of tert. butyl hydroperoxide (t-BuOOH). After stirring for 25 min a solution of 9 mg ($2.3 \times 10^{-5}$ moles) of 3,5-cyclovitamin $D_3$ (compound 2a, prepared from vitamin $D_3$ (1a) by the method of Sheves & Mazur, J. Am. Chem. Soc. 97, 6249 (1975)) in 0.5 ml of $CH_2Cl_2$ is added dropwise. The mixture is stirred at room temperature for an additional 25 min. Then 2.0 ml of 10% NaOH is added, and this resulting mixture is diluted with 15 ml of diethylether. The organic phase is separated and washed successively with 10% NaOH ($2 \times 10$ ml), $H_2O$ ($2 \times 10$ ml), sat. $FeSO_4$ ($3 \times 10$ ml), and sat. NaCl (15 ml); and then dried over $MgSO_4$. Removal of solvent in vacuo yields a crude oily product that after chromatography on a silica gel thin layer plate ($10 \times 20$ cm, 750 μm) developed in 30% ethylacetate: Skellysolve B yields 4.5 mg (43% yield) of 1α-hydroxy-3,5-cyclovitamin $D_3$ (3a): mass spectrum: (m/e) 414(30), 382(70), 341(35), 269(20), 247(45), 174(25), 165(30), 135(65); NMR, δ, 0.53 (3H, s, 18-$H_3$), 0.61 (2H, m, 4-$H_2$), 0.87 (6H, d, 26-$H_3$ and 27-$H_3$), 0.92 (3H, d, 21-$H_3$), 3.26 (3H, s, 6-$OCH_3$), 4.18 (1H, d, J=9.0 Hz, 6-H), 4.22 (1H, m, 1-H), 4.95 (1H, d, J=9 Hz, 7-H), 5.17 (1H, d, J=2.2 Hz, 19(Z)-H), 5.25 (1H, d, J=2.2 Hz, 19(E)-H).

As a minor component 2.0 mg (19% yield) of 1-oxo-cyclovitamin $D_3$ (7a) was isolated from the reaction mixture: mass spectrum: (m/e) 412 (40), 380 (50), 267 (15), 247 (23), 135 (50), 133 (100); NMR, δ, 0.49 (3H, s, 18-$H_3$), 0.58 (2H, m, 4-$H_2$), 0.87 (6H, d, 26-$H_3$ and 27-$H_3$), 0.93 (3H, d, 21-$H_3$), 3.30 (3H, s, 6-OCH$_3$), 4.07 (1H, d, J=9.0 Hz, 6-H), 5.02 (1H, d, J=9.0 Hz, 7-H), 5.62 (1H, s, 19(Z)-H), 6.04 (1H, s, 19(E)-H); UV 248 (4,000).

EXAMPLE 2

1α-Acetoxy-cyclovitamin $D_3$ (4a)

Compound 3a (1.5 mg) is dissolved in 200 μl of dry pyridine and 50 μl of acetic anhydride. The reaction is kept at room temperature overnight, then diluted with 5 ml of sat. NaHCO$_3$ solution. This solution is extracted with three 5 ml portions of ether and the organic extracts are washed with H$_2$O (2×10 ml), dried over MgSO$_4$, and the solvent is removed in vacuo to give compound 4a: NMR, δ, 0.53 (3H, s, 18-$H_3$), 0.69 (2H, m, 4-$H_2$), 0.87 (6H, d, 26-$H_3$ and 27-$H_3$), 0.92 (3H, d, 21-$H_3$), 2.10 (3H, s, 1-OAc), 3.26 (3H, s, 6-OCH$_3$), 4.18 (1H, d, J=9.2 Hz, 6-H), 4.98 (1H, d, J=9.2 Hz, 7-H), 4.98 (1H, d, J=2.1 Hz, 19(Z)-H), 5.23 (1H, m, 1-H), 5.25 (1H, d, J=2.1 Hz, 19(E)-H).

EXAMPLE 3

1α-Hydroxyvitamin $D_3$ (6a)

A solution of 1.3 mg of (4a) in 0.5 ml of a 3:1 mixture of 1,4-dioxane and H$_2$O is heated to 55°, 0.2 mg of p-toluenesulfonic acid in 4 μl of H$_2$O is added and heating is continued for 0.5 hr. The reaction is then quenched with 2 ml of sat. HaHCO$_3$ and extracted with two 10 ml portions of ether. The organic extracts are dried over MgSO$_4$ and the solvent removed in vacuo. The crude product is then applied to a 10×20 cm silica gel plate developed in 30% EtOAc: Skellysolve B to yield 400 μg of product 5a: UV, $\lambda_{max}$ 264 nm; mass spectrum, m/e 442 (M$^+$, 75), 382(70), 269(15), 134(100); NMR, δ, 0.52 (3H, s, 18-$H_3$), 0.86 (6H, d, J=5.5 Hz, 26-$H_3$ and 27-$H_3$), 0.91 (3H, d, J=5.9 Hz, 21-$H_3$), 2.03 (3H, s, 1-OCOCH$_3$), 4.19 (1H, m, 3-H), 5.04 (1H, d, J=1.5 Hz, 19(Z)-H), 5.31 (1H, m(sharp), 19(E)-H), 5.49 (1H, m, 1-H), 5.93 (1H, d, J=11.4 Hz, 7-H), 6.37 (1H, d, J=11.4 Hz, 6-H).

Product 5a is taken up in 0.5 ml of ether and treated with excess LiAlH$_4$. The reaction is quenched with sat. NaCl solution and product is isolated by filtration and evaporation of the solvent in vacuo. The single product (6a) co-chromatographs with a standard sample of 1α-hydroxyvitamin $D_3$ in 97:3 CHCl$_3$:CH$_3$OH (1α-hydroxyvitamin $D_3$ $R_f$=0.10, 1β-hydroxyvitamin $D_3$ $R_f$=0.15, reaction product (6a), $R_f$=0.10). This product possesses $\lambda_{max}$=264 nm and a mass spectrum and nmr spectrum identical to that of authentic 1α-hydroxyvitamin $D_3$.

EXAMPLE 4

25-Hydroxycyclovitamin $D_3$ (2b)

A solution of 100 mg of 25-hydroxyvitamin $D_3$ (1b) and 150 mg of p-toluene-solfonyl chloride in 0.5 ml of dry pyridine is allowed to react for 24 hr at 3°, and is then quenched with 5 ml of sat. NaHCO$_3$. The aqueous phase is extracted with ether (2×10 ml) and the ether extract is washed with sat. NaHCO$_3$ (3×10 ml), 3% HCl (2×10 ml), and H$_2$O (2×10 ml) and then dried over MgSO$_4$. The solvent is removed in vacuo and the crude residue (25-hydroxyvitamin $D_3$ 3-tosylate) is taken up in 1.5 ml of anhydrous methanol and 0.3 ml of anhydrous acetone; 170 mg (8 eq.) of NaOAc is added and the solution is warmed to 55° for 20 hr. The mixture is cooled, diluted with 10 ml of H$_2$O and extracted with 3×10 ml of ether. The organic extracts are washed with three 10 ml portions of H$_2$O, dried over MgSO$_4$, and the solvent is removed in vacuo. This crude residue is applied to a 20 cm×20 cm silica gel TLC plate (750 μm thick) which is developed once in a Skellysolve B:ethyl acetate (8:2) system to yield 48 mg (45% overall yield from 1b) of (2b): mass spectrum, m/e: 414 (M$^+$, 40), 399(10), 382(80), 253(50), 59(100); NMR, δ, 0.53 (3H, s, 18-$H_3$), 0.74 (2H, m, 4-$H_2$), 0.94 (3H, d, J=6.2 Hz, 21-$H_3$), 1.21 (6H, s, 26-$H_3$ and 27-$H_3$), 3.25 (3H, s, 6-OCH$_3$), 4.16 (1H, d, J=9.2 Hz, 6-H), 4.89 (1H, m(sharp), 19(Z)-H), 4.99 (1H, d, J=9.3 Hz, 7-H), 5.04 (1H, m(sharp), 19(E)-H).

EXAMPLE 5

1α,25-Dihydroxycyclovitamin $D_3$ (3b) and 1-oxo-25-hydroxycyclovitamin $D_3$ (7b)

A mixture of 2.45 mg (0.5 eq.) of SeO$_2$, 14 μl (2 eq.) of t-BuOOH and 1.2 ml of dry CH$_2$Cl$_2$ is allowed to react at room temperature for 30 min. A solution of the cyclovitamin (2b) in 0.5 ml of CH$_2$Cl$_2$ is added dropwise to this oxidizing medium, and the reaction is continued for 15 min. The reaction is then quenched with 2.0 ml of 10% NaOH and diluted with 20 ml of diethyl ether. The organic phase is separated and washed successively with 10% NaOH, H$_2$O, sat. FeSO$_4$ solution, sat. NaHCO$_3$, and again with H$_2$O, and then dried over MgSO$_4$. The solvent is removed in vacuo and the crude residue is applied to a silica gel thin layer plate (20 cm×20 cm, 750μm thick), which is developed in a Skellysolve B:ethyl acetate (6:4) system to yield 11 mg (53% yield) of (3b): mass spectrum: m/e 430(M$^+$, 15), 412(12), 380(35), 269(10), 59(100); NMR, δ, 0.53 (3H, s, 18-$H_3$), 0.61 (2H, m, 4-$H_2$), 0.93 (3H, d, J=6.2 Hz, 21-$H_3$), 1.21 (6H, s, 26-$H_3$ and 27-$H_3$), 3.25 (3H, s, 6-OCH$_3$), 4.17 (1H, d, J=9.2 Hz, 6-H), 4.20 (1H, m, 1-H), 4.95 (1H, d, J=9.2 Hz, 7-H), 5.19 (1H, d, J=1.9 Hz, 19(Z)-H), 5.22 (1H, d, J=1.9 Hz, 19(E)-H). As a minor component 1-oxo-25-hydroxycyclovitamin $D_3$ (7b) was isolated (15%) from the reaction mixture. Mass spectrum: m/e 428 (M$^+$).

EXAMPLE 6

1α,25-Dihydroxycyclovitamin $D_3$-1,25-diacetate (4b-25-OAc)

A solution of 7 mg of (3b) in 200 μl of dry pyridine is treated with 10 μl of acetic anhydride. The system is flushed with N$_2$ and heated to 97° for 16.0 hr. After cooling, the mixture is diluted with 5 ml of sat. NaHCO$_3$. The aqueous mixture is extracted with two 10 ml portions of ether and the organic phase is washed successively with two 10 ml portions of sat. NaHCO$_3$, and then with 10 ml of H$_2$O. After drying over MgSO$_4$, the solvent and residual pyridine are removed by azeotropic distillation with benzene in vacuo. The crude product is then applied to a silica gel thin layer plate (10 cm×20 cm, 750μm thick) developed in Skellysolve B:ethyl acetate (8:2) to yield 6 mg (72%) of the diacetate (4b,25-OAc) and 1.2 mg of the corresponding 3-acetoxy-25-hydroxy derivative.

EXAMPLE 7

1α,25-Dihydroxyvitamin D$_3$-1,25-diacetate (5b,25-OAc)

To 3.8 mg of (4b,25-OAc), dissolved in 400 μl of dioxane:H$_2$O (3:1) and warmed to 55°, is added 8 μl of a solution of p-toluene sulfonic acid in H$_2$O and heating is continued for 10 min. The reaction is quenched with sat. NaHCO$_3$ and extracted with two 10 ml portions of ether. The ether solution is washed with two 10 ml portions of H$_2$O and dried over MgSO$_4$. The solvent is removed in vacuo, and the residue is applied to a silica gel thin layer plate (5×20 cm, 250 μm thick) which is developed in Skellysolve B:ethyl acetate (8:2) to yield 1.8 mg (45%) of (5b,25-OAc): UV; $\lambda_{max}$ 265 nm; mass spectrum: m/e 500(M$^+$, 25), 440(55), 422(15), 398(10), 380(45), 134(100); NMR, δ, 0.52 (3H, s, 18-H$_3$), 0.92 (3H, d, J=6.2 Hz, 21-H$_3$), 1.42 (6H, s, 26-H$_3$ and 27-H$_3$), 1.97 (3H, s, 25-OCOCH$_3$), 2.03 (3H, s, 1-OCOCH$_3$), 4.18 (1H, m, 3-H), 5.03 (1H, d, J=1.1 Hz, 19(Z)-H), 5.31 (1H, m(sharp), 19(E)-H), 5.49 (1H, m, 1-H), 5.93 (1H, d, J=11.4 Hz, 7-H), 6.37 (1H, d, J=11.4 Hz, 6-H).

EXAMPLE 8

1α,25-Dihydroxyvitamin D$_3$ (6b)

To a stirred solution of 1.0 mg of the diacetate, (5b,25-OAc) in 1.5 ml of ether is added 0.5 ml of an ether solution saturated with LiAlH$_4$. After 10 min at room temperature, the reaction is quenched with sat. NaCl solution and the salts are dissolved by addition of 3% HCl. The aqueous phase is extracted with ether and the ether extracts are washed with H$_2$O and dried over MgSO$_4$. Thin layer chromatography (5×20 cm silica gel plates, 250 μm thick) using 5% MeOH: CHCl$_3$ yields 0.6 mg (70%) of 1α,25-dihydroxyvitamin D$_3$ (6b), exhibiting a UV-spectrum with $\lambda_{max}$ 265 nm. The identity of 6b as 1α,25-dihydroxyvitamin D$_3$ is established by direct comparison of mass and nmr spectra with those of authentic material, as well as by co-chromatography of 6b with authentic 1α,25-dihydroxyvitamin D$_3$.

EXAMPLE 9

Cyclovitamin D$_2$ (2c)

A solution of 100 mg of vitamin D$_2$ (1c) and 100 mg of p-toluenesulfonyl chloride in 0.3 ml of pyridine is allowed to react for 24 hr at 3°, and is then quenched with 10 ml of sat. NaHCO$_3$. The aqueous mixture is extracted with two 10 ml portions of ether and the ether extract is washed successively with sat. NaHCO$_3$ (3×10 ml), 3% HCl (2×10 ml), and H$_2$O (2×10 ml), and is then dried over MgSO$_4$. The solvent is removed in vacuo and the crude vitamin D$_2$-3-tosylate is taken up in 1.5 ml of anhydrous methanol and 0.3 ml of anhydrous acetone. After addition of 170 mg of sodium acetate, the solution is warmed to 55° for 20 hr. After cooling, the solution is diluted with 10 ml of H$_2$O and extracted with three 10 ml portions of ether. The organic extracts are washed with three 10 ml portions of H$_2$O, dried with MgSO$_4$, and the solvent is removed in vacuo. The residue is chromatographed on a silica gel thin layer plate (20×20 cm, 750μm) in Skellysolve B:ethyl acetate (8:2) to yield 60 mg (59%) of (2c): mass spectrum: m/e 410(M$^+$, 15), 378(40), 253(40), 119(60); NMR, δ, 0.55 (3H, s, 18-H$_3$), 0.74 (2H, m, 4-H$_2$), 0.82 and 0.84 (6H, dd, J=4.1 Hz, 26-H$_3$ and 27-H$_3$), 0.91 (3H, d, J=7.0 Hz, 21-H$_3$), 1.02 (3H, d, J=6.6 Hz, 28-H$_3$), 3.26 (3H, s, 6-OCH$_3$), 4.13 (1H, d, J=9.6 Hz, 6-H), 4.89 (1H, m, 19(Z)-H), 5.00 (1H, d, J=9.4 Hz, 7-H), 5.04 (1H, m(sharp), 19(E)-H), 5.20 (2H, m, 22-H and 23-H).

EXAMPLE 10

1α-Hydroxycyclovitamin D$_2$ (3c) and 1-oxo-cyclovitamin D$_2$ (7c)

A mixture of 2.7 mg of SeO$_2$ and 13.4 μl of 70% t-BuOOH, in 1.5 ml of dry CH$_2$Cl$_2$, is allowed to react for 30 min. Compound 2c (20 mg) in 0.5 ml of CH$_2$Cl$_2$ is then added dropwise, the reaction is continued for 15 min, and then quenched with 2.0 ml of 10% NaOH. The solution is diluted with 15 ml of ether, the ether phase is separated and washed successively with 10% NaOH, H$_2$O, sat. FeSO$_4$ solution, sat. NaHCO$_3$, and again with H$_2$O. After drying over MgSO$_4$, the solvent is removed in vacuo, and the residue is applied to a silica gel thin layer plate (20×20 cm, 750 μm) which is developed once in Skellysolve B:ethyl acetate (8:2) system to yield 9.5 mg (45%) of (3c): mass spectrum: m/e 426(M$^+$, 55), 394(75), 353(30), 269(40), 135(95); NMR, δ, 0.53 (3H, s, 18-H$_3$), 0.63 (2H, m, 4-H$_2$), 0.82 and 0.84 (6H, dd, 26-H$_3$ and 27-H$_3$), 0.92 (3H, d, J=6.0 Hz, 21-H$_3$), 1.02 (3H, d, J=6.4 Hz, 28-H$_3$), 3.26 (3H, s, 6-OCH$_3$), 4.18 (1H, d, J=9.6 Hz, 6-H), 4.21 (1H, m, 1-H), 4.94 (1H, d, J=9.6 Hz, 7-H), 5.17 (1H, m(sharp), 19(Z)-H), 5.19 (2H, m, 22-H and 23-H), 5.24 (1H, m(sharp), 19(E)-H). A second minor component isolated from the reaction mixture proved to be 1-oxo-cyclovitamin D$_2$ (7c): mass spectrum, m/e 424 (M$^+$).

EXAMPLE 11

1α-Hydroxycyclovitamin D$_2$-1-acetate (4c)

To 6.5 mg of (3c) in 300 μl of dry pyridine is added 150 μl of acetic anhydride. This solution is heated to 55° for 1.5 hr, then diluted with 5 ml of sat. NaHCO$_3$ and extracted with two 10 ml portions of ether. The organic extracts are washed with sat. NaHCO$_3$, and H$_2$O, dried over MgSO$_4$ and the residual pyridine and solvent is removed by azeotropic distillation with benzene in vacuo, to yield compound 4c: mass spectrum: m/e 468(M$^+$, 40), 408(20), 376(65), 251(60), 135(100).

EXAMPLE 12

1α-Hydroxyvitamin D$_2$-1-acetate (5c)

A solution of 5.0 mg of (4c) in 400 μl of dioxane: H$_2$O (3:1) is heated to 55°; 12 μl of an aqueous solution of p-toluenesulfonic acid (50 μg/μl) is added and heating is continued for 10 min. The reaction is then quenched with sat. NaHCO$_3$ and extracted with two 10 ml portions of ether. The separated ether phase is washed with 10 ml of sat. NaHCO$_3$ and two 10 ml portions of H$_2$O, dried over MgSO$_4$, and the solvent is removed in vacuo. Preparative thin layer chromatography on silica gel (Skellysolve B:ethyl acetate, 8:2) gives 1.6 mg of 5c (32%) yield); UV; $\lambda_{max}$ 265 nm; mass spectrum: m/e 454(M$^+$, 80), 394(80), 376(20), 269(40), 135(100); NMR, δ, 0.53 (3H, s, 18-H$_3$), 0.81 and 0.84 (6H, d, J=4.4 Hz, 26-H$_3$ and 27-H$_3$), 0.91 (3H, d, J=7.0 Hz, 21-H$_3$), 1.01 (3H, d, J=6.7 Hz, 28-H$_3$), 2.03 (3H, s, 3-OCOCH$_3$), 4.18 (1H, m, 3-H), 5.03 (1H, d, J=1.5 Hz, 19(Z)-H), 5.19 (2H, m, 22-H and 23-H), 5.3 (1H, m(sharp), 19(E)-H), 5.48 (1H, m, 1-H), 5.92 (1H, d, J=11.0 Hz, 7-H), 6.37 (1H, d, J=11.0 Hz, 6-H).

EXAMPLE 13

1α-Hydroxyvitamin D$_2$ (6c)

A solution of 1.1 mg of (5c) in 1.5 ml of ether is treated with 0.5 ml of an ether solution saturated with LiAlH$_4$. After 10 min at room temperature the reaction is quenched with sat. NaCl and the salts dissolved in 3% HCl. This aqueous solution is extracted with ether and the organic extracts are washed with water and dried over MgSO$_4$. TLC on 250μ thick, 5×20 cm, plates in 5% methanol:chloroform yields 0.8 mg (75% yield) of 1α-hydroxy-vitamin D$_2$: UV: λ$_{max}$ 265 nm; mass spectrum: m/e 412(M+), 394, 376, 287, 269, 251, 152, 134 (base peak); NMR: δ, 0.56 (3H, s, 18-H$_3$), 0.82 and 0.84 (6H, dd, J=4.4 Hz, 26-H$_3$ and 27-H$_3$), 0.92 (3H, d, J=6.6 Hz, 21-H$_3$), 1.02 (3H, d, J=6.6 Hz, 28-H$_3$), 4.23 (1H, m, 3-H), 4.42 (1H, m, 1-H), 5.00 (1H, m(sharp), 19(Z)-H), 5.20 (2H, m, 22-H and 23-H), 5.32 (1H, dd, J=1.4 Hz, 19(E)-H), 6.02 (1H, d, J=11.1 Hz, 7-H), 6.38 (1H, d, J=11.6 Hz, 6-H). These spectral data are in full accord with data obtained for 1α-hydroxyvitamin D$_2$, prepared by an entirely different method [Lam et al. Science, 186, 1038–1040 (1974)].

EXAMPLE 14

Solvolysis of 1α-Acetoxycyclovitamin D in Acetic Acid

A solution of 3.0 mg of 1α-hydroxycyclovitamin D$_3$-1-acetate (4a) in 200 μl of glacial acetic acid is warmed to 55° for 15 min and subsequently quenched with ice-cold sat. NaHCO$_3$. The aqueous mixture is extracted with diethylether and the organic phase is washed with sat. NaHCO$_3$ and water, dried over MgSO$_4$, and filtered to yield a solution of 5,6-cis and 5,6-trans-1α-acetoxyvitamin D$_3$ 3-acetates (UV: λ$_{max}$ 267–269 nm). The dried ether solution is treated with a small amount (1.0 mg) of lithium aluminum hydride, quenched with sat. NaCl, filtered and the solvent is removed in vacuo. The crude oil is applied to a 5×20 cm silica gel tlc plate (250 μm thick) which is developed in 5% methanol:chloroform to yield 1.6 mg of a mixture (UV, λ$_{max}$ 267–269 nm) of 1α-hydroxyvitamin D$_3$ (6a) and the corresponding 5,6-trans isomer (5,6-trans-1α-hydroxyvitamin D$_3$) in a ratio of 3:1 as determined by NMR analysis: Characteristic resonances for the cis isomer (6a): δ, 6.38 and 6.01 (d, J=11.4 Hz, 6-H and 7-H), 5.33 (dd, J=1.5 Hz, 19(E)-H), 5.01 (sharp m, 19(Z)-H), 0.54 (s, 18-H$_3$); for the 5,6-trans isomer: 6.58 and 5.88 (d, J=11.4 Hz, 6-H and 7-H), 5.13 (d, J=1.4 Hz, 19(E)-H), 4.98 (sharp m, 19(Z)-H), 0.56 (s, 18-H$_3$).

The same procedure may be used to effect the cleavage of the cyclorane ring (cycloreversion) of other cyclovitamins or their C-1-oxygenated analogs. Thus heating 1α-acetoxy-25-hydroxyvitamin D$_3$ (compound 4b, no protecting group required for 25-OH function) in glacial acetic acid as described above, yields 1α-acetoxy-25-hydroxyvitamin D$_3$ 3-acetate as the major product (plus some of the corresponding 5,6-trans isomer, as minor product) and this mixture may be directly hydrolyzed (MeOH/KOH) or subjected to hydride reduction as described above, to yield 1α,25-dihydroxyvitamin D$_3$ as the major product and 5,6-trans-1α,25-dihydroxyvitamin D$_3$ as a minor product.

EXAMPLE 15

Formic acid catalyzed solvolysis of 1α-acetoxycyclovitamin D$_3$

A solution of the 1α-acetoxycyclovitamin D$_3$ (4a) in dry dioxane is warmed to 55° and treated with a 1:1 solution of 98% formic acid:dioxane (50 μl/mg cyclovitamin) for 15 min. The reaction is then quenched with ice-water and extracted with ether. The ether extracts are washed with water, sat. NaHCO$_3$, sat. NaCl, dried over MgSO$_4$, and the solvent removed in vacuo. The crude product (1α-acetoxy-3β-formylvitamin D$_3$ and its 5,6-trans isomer) is dissolved in a 1:1 solution of dioxane:methanol and an equivalent amount of aqueous K$_2$CO$_3$ (10 mg/100 μl) is added. After 5 min at room temperature, the solution is diluted with water and extracted repeatedly with ether. The ether extracts are washed with water, dried over MgSO$_4$, and the solvent is removed in vacuo. The crude cis and trans mixture of 1-acetoxy-3-hydroxyvitamins is then chromatographed on a 10×20 cm, 750$_{μm}$ thick silica gel plate in 1:3 ethyl acetate:Skellysolve B to yield the pure cis-1α-acetoxyvitamin D$_3$. Basic hydrolysis, (NaOH in methanol) yields a product which is chromatographically and spectrally identical to an authentic sample of 1α-hydroxyvitamin D$_3$.

EXAMPLE 16

Cyclovitamin D$_3$ (2a) by NaHCO$_3$-buffered solvolysis of vitamin D$_3$-tosylate To a suspension of 170 mg of vitamin D$_3$-tosylate in 6.0 ml of anhydrous methanol is added 213 mg (8.0 eq.) of NaHCO$_3$. The system is flushed with nitrogen and heated to 58° for 20 hr. The reaction is then diluted with sat. NaCl solution, transferred to a separatory funnel and extracted with 2×10 ml portions of Et$_2$O. The organic extracts are washed with 1×10 ml portion of sat. NaCl and dried over MgSO$_4$. After removal of the solvent in vacuo, the oily residue is chromatographed on a 750 μm, 20×20 cm silica gel prep plate in ethyl acetate:Skellysolve B 2:8 to yield 94 mg (75%) of cyclovitamin D$_3$ (2a).

EXAMPLE 17

6-Hydroxy-cyclovitamin D$_3$ (8a)

A solution of 100 mg of vitamin D$_3$, 100 mg of TsCl and 500 μl of dry pyridine is kept at 5° for 24 hr then diluted with ether and washed several times with sat. NaHCO$_3$. The organic layer is dried over MgSO$_4$ and the solvent is removed in vacuo. The crude D$_3$-tosylate is suspended in 4.0 ml of acetone:H$_2$O 9:1 along with 175 mg (8 eq.) of NaHCO$_3$. The resulting mixture is heated at 55° overnight, diluted with sat. NaCl and extracted twice with ether. The ether extract is washed once with water, dried over MgSO$_4$, and the solvent reoved in vacuo. Preparative TLC (20×20 cm, 750 μm, 8:2 Skellysolve B: ethyl acetates yields 55 mg of the 6-hydroxy-3,5-cyclovitamin D$_3$ (8a); mass spectrum, m/e 384 (M+), 366, 253, 247.

EXAMPLE 18

6-Acetoxyvitamin D$_3$ (9a)

To a solution of 300 μl of dry pyridine and 200 μl of Ac$_2$O is added 6 mg of 6-hydroxy-cyclovitamin D$_3$ (8a) in 200 μl of pyridine. The reaction is warmed at 55° for 2.0 hr under N$_2$ then diluted with a large excess of toluene. The solution is evaporated to dryness at 40° in vacuo to yield the crude 6-acetoxycyclovitamin $D_3$ (9a); mass spectrum, m/e 426 (M+).

EXAMPLE 19

Hydride reduction of 1-oxo-cyclovitamin $D_3$ (7a) to 3a

A solution of 2.0 mg of 1-oxo-cyclovitamin $D_3$ in 500 μl of ether is treated with 300 μl of ether saturated with $LiAlH_4$. After 30 min the reaction is carefully quenched by the dropwise addition of sat. NaCl. The insoluble salts are removed by filtration and the filtrate is dried over $MgSO_4$. The solvent is removed in vacuo to yield 1.7 mg of a 95:5 mixture of 1α-hydroxycyclovitamin $D_3$ (3a) and the corresponding 1β-hydroxycyclovitamin $D_3$ isomer, which are separated by chromatography. Similar treatment of 1-oxocyclovitamin $D_3$ with 300 μl of 100% ethanol saturated with $NaBH_4$ yields an 8:2 mixture of 1α-hydroxy and 1β-hydroxycyclovitamin $D_3$ compounds (3a and its 1β-epimer).

EXAMPLE 20

$SeO_2$/t-BuOOH oxidation of 6-hydroxy cyclovitamin $D_3$ (8a)

To a stirring suspension of 2.0 mg of $SeO_2$ in 1.5 ml dry $CH_2Cl_2$ is added 10 μl of 70% t-BuOOH. When homogeneous, a solution of 14 mg of 6-hydroxy-cyclovitamin $D_3$ (8a) in 500 μl of dry $CH_2Cl_2$ is added dropwise and the reaction is continued for 1.5 hr at room temperature. The reaction is quenched with 10% NaOH, diluted with ether, washed with 10% NaOH and water, dried over $MgSO_4$, and the solvent removed in vacuo. The crude oily residue is chromatographed (10×20 cm, 750 μm, 1:1 ethyl acetate:Skellysolve B) to yield 1.5 mg (10%) 1-oxo-6-hydroxy-cyclovitamin $D_3$: mass spectrum, (m/e), 398 (35), 380 (25), 247 (25), 135 (40), 133 (100); 2.0 mg (15%) of 1α, 6-dihydroxy cyclovitamin $D_3$ (10a): mass spectrum; (m/e), 400 (50), 382 (80), 269 (20), 247 (40), 135 (80), 133 (40); and 2.0 mg (15%) of 1α-hydroxyvitamin $D_3$ (6a), and the corresponding 1α-hydroxy-5,6-trans isomer.

EXAMPLE 21

Conversion of 1α, 6-dihydroxy-cyclovitamin $D_3$ (10a) to 1 α-hydroxyvitamin $D_3$ (6a)

A solution of 400 μl dry pyridine, 200 μl acetic anhydride, and 2.0 mg of 1α, 6-dihydroxy-cyclovitamin $D_3$ (10a) is warmed to 55° for 2.0 hr. The reaction is then diluted with toluene and stripped to dryness. The resulting oil (1α,6-diacetoxy-cyclovitamin $D_3$) is taken up in 100 μl of THF and treated with 200 μl of 97% $HCO_2H$ for 15 min at 55°. Dilution with sat. NaCl, extraction with ether, washing with sat. $NaHCO_3$, drying over $MgSO_4$, and removal of the ether in vacuo gives the crude 1-acetoxy-3-formate cis- and trans- vitamin derivatives. Selective formate hydrolysis with $K_2CO_3$ followed by chromatography yields pure 1α-acetoxyvitamin $D_3$ (5a) which is converted to 1α-hydroxyvitamin $D_3$ (6a) by simple KOH/MeOH hydrolysis.

EXAMPLE 22

24(R),25-Dihydroxy-cyclovitamin $D_3$ (2d)

To 150 μl of dry pyridine is added 10.4 mg of 24R,25-$(OH)_2D_3$ and 7.13 mg (1.5 eq.) of TsCl. The reaction is maintained at 0° for 72 hr then diluted with sat. $NaHCO_3$ and extracted with ether. After washing the ether extract with sat. $NaHCO_3$, drying over $MgSO_4$, and removing the solvent in vacuo, the crude tosylate (~70% by TLC) is suspended in 2 ml of anhydrous MeOH along with 25 mg of $NaHCO_3$ and heated under $N_2$ at 58° for 20 hr. The reaction is then diluted with sat. NaCl and extracted with ether. The ether extracts are washed with water, dried over $MgSO_4$ and the solvent removed in vacuo. Preparative TLC (10×20 cm, 750 μm silica gel, 6:4 Skellysolve B:ethyl acetate) yields 2.5 mg of recovered 24R,25-$(OH)_2D_3$ and 4.4 mg of 24R,25-dihydroxy-cyclovitamin D (2d): mass spectrum, (m/e), 430 (15), 398 (65), 253 (40), 159 (45), 119 (55), 59 (100); NMR, δ, 0.55 (3H, s, 18-$H_3$), 0.74 (2H, m, 4-$H_2$), 0.94 (3H, d, J=6.2 Hz, 21-$H_3$), 1.17 (3H, s, 26-$H_3$), 1.22 (3H, s, 27-$H_3$), 3.26 (3H, s, 6-$OCH_3$), 3.34 (1H, m, 24-H), 4.17 (1H, d, J=9.0 Hz, 6-H), 4.88 (1H, m(sharp), 19(Z)-H), 5.00 (1-H, d, J=9.0 Hz, 7-H), 5.04 (1H, m(sharp), 19(E)-H).

EXAMPLE 23

1α,24(R),25-Trihydroxy-cyclovitamin $D_3$ (3d)

To a previously prepared solution of 1.12 mg $SeO_2$ and 12 μl of 70% t-BuOOH in 1.0 ml of dry $CH_2Cl_2$ is added 4.2 mg of 24R,25-dihydroxy-cyclovitamin $D_3$ in 500 μl of $CH_2Cl_2$. After 30 min an addition portion of 1.12 mg $SeO_2$ and 12 μl 70% t-BuOOH, in 500 μl of $CH_2Cl_2$ is added and the reaction continued for an hour longer. The reaction is quenched with 10% NaOH, diluted with ether, and washed twice with 10% NaOH followed by a water wash. The organic solution is dried over $MgSO_4$, the solvent removed in vacuo, and the resulting oil is chromatographed on a 5×20 cm, 250 μm silica gel plate in ethyl acetate:Skellysolve B 1:1 to yield 1.6 mg of 1α,24(R),25-trihydroxycyclovitamin $D_3$ (3d): mass spectrum, (m/e), 446 (30), 414 (50), 396 (40), 269 (30), 135 (80), 59 (100); NMR, δ, 0.55 (3H, s, 18-$H_3$), 0.65 (2H, m, 4-$H_2$), 0.96 (3H, d, J=6.0 Hz, 21-$H_3$), 1.19 (3H, s, 26-$H_3$), 1.24 (3H, s, 27-$H_3$), 3.28 (3H, s, 6-$OCH_3$), 3.35 (1H, m, 24-H), 4.20 (1H, d, J=9.0 Hz, 6-H), 4.22 (1H, m, 1-H), 4.97 (1H, d, J=9.0 Hz, 7-H), 5.18 (1H, m(sharp), 19(Z)-H), 5.26 (1H, d, J=2.2 Hz, 19(E)-H). 1-oxo-24(R),25-dihydroxy-cyclovitamin $D_3$ (7d) is also isolated as a minor component (<20%).

EXAMPLE 24

1α,24(R),25-Trihydroxyvitamin $D_3$ (6d)

To 200 μl of dry pyridine and 150 μl of $Ac_2O$ is added 1.4 mg of 1α,24R,25-trihydroxy-cyclovitamin $D_3$ (3d). The system is flushed with $N_2$ and heated to 95° for 20 hr. The reaction is then diluted with dry toluene and azeotropically distilled to dryness. The oily product, 1α,24(R),25-triacetoxycyclovitamin $D_3$ (4d-24,25-diacetate), is dissolved in 200 μl of THF and added to 500 μl of a 1:1 solution of 97% $HCO_2H$:THF and heated to 55° for 15 min. The cooled reaction is diluted with ether, washed with $H_2O$, sat. $NaHCO_3$, sat. NaCl, and dried over $MgSO_4$. After removal of the solvent in vacuo the crude 1α,24R,25-triacetoxy-3β-formate vitamin D intermediate is dissolved in 200 μl of THF and treated with 1.0 mg $K_2CO_3$ in 10 μl $H_2O$ and 90 μl MeOH for 5 min at room temperature. Dilution with sat. NaCl, extraction with ether, and chromatography on a 5×20 cm, 250 μm, silica gel plate in ethyl acetate: Skellysolve B 4:6 yields 1α,24R,25-triacetoxy-vitamin $D_3$. Treatment of this triacetate with $LiAlH_4$ gives 1α,24R,25-trihydroxyvitamin $D_3$ (6d) which is identical in all respects to an authentic sample.

EXAMPLE 25

Conversion of 1-hydroxycyclovitamin $D_3$ (3a) to 1α-hydroxyvitamin $D_3$ (6a) via the 1-formyl intermediate (11a)

A 200 μl portion of acetic anhydride is cooled to 0° and 100 μl of 97% formic acid is added slowly. The solution is briefly (15 min) heated to 50° then cooled to 0°. A 100 μl portion of the acetic-formic anhydride is then added to a solution of 5 mg of 1α-hydroxycyclovitamin $D_3$ (3a) in pyridine at 0°. After 2.0 hr the reaction is diluted with sat. NaCl, extracted with ether, washed with $H_2O$, and dried over $MgSO_4$. The crude 1α-formylcyclovitamin $D_3$ (11a) obtained after removing the solvent in vacuo is dissolved in glacial acetic acid and heated to 55° for 15 min. Dilution with sat. NaCl, extraction with ether, and isolation of the organic products give the crude product consisting of 1-formyloxyvitamin $D_3$ 3-acetate (12a) and the corresponding 5,6-trans isomer. Treatment of the crude mixture with $K_2CO_3$ in $H_2O$/MeOH followed by chromatography (5×20 cm, 250 μm, silica gel, 3:7 ethyl acetate:-Skellysolve B) yields the pure 1α-hydroxyvitamin $D_3$ 3-acetate and 5,6-trans 1α-hydroxyvitamin $D_3$ 3-acetate, which are hydrolytically converted (KOH/MeOH) to the corresponding 1α-hydroxy-vitamin $D_3$ (6a) and its 5,6-trans isomer respectively.

EXAMPLE 26

Crown ether catalyzed cycloreversion of 1α-acetoxy-cyclovitamin $D_3$

A 0.5 M hexane:benzene (1:1) solution of 15-crown-5 (Aldrich Chemical Co., Milwaukee) is saturated with finely divided anhydrous sodium acetate. To 300 μl of this solution is added 11.0 mg of 1α-acetoxycyclovitamin $D_3$ (4a) in 600 μl of dry hexanes followed by 200 μl of 97% formic acid. The two-phase mixture is vortexed occasionally over 30 min, then diluted with hexanes and the acid layer removed. The organic phase is washed with sat. $NaHCO_3$, sat. NaCl, dried over $MgSO_4$ and the solvent removed in vacuo. The crude oil is taken up in 300 μl of THF and 300 μl of methanol and treated with 10 mg of $K_2CO_3$ in 100 μl of $H_2O$. After 5 min at ambient temperature the reaction is diluted with sat. NaCl and extracted with two portions of ether. The organic layer is washed with $H_2O$, dried over $MgSO_4$, and the solvent removed in vacuo. The resulting mixture is subjected to preparative TLC (750 μm, 10×20 cm, 75:25 Skellysolve B:ethyl acetate) to yield 5.7 mg (54%) of 1α-acetoxy-vitamin $D_3$ (5a) and 2.1 mg (20%) of 5,6-trans-1α-acetoxy-vitamin $D_3$.

EXAMPLE 27

Conversion of 1α-hydroxyvitamin $D_3$ (6a) to 1α-hydroxycyclovitamin $D_3$ (3a)

To 0.2 ml of pyridine is added 3.0 mg of 1α-acetoxyvitamin $D_3$ (5a), obtained by either selective acetylation of 1α-hydroxyvitamin $D_3$ (3a)(2 molar excess acetic anhydride in pyridine, 4 hours, room temperature, followed by separation of the desired 1α-acetoxyvitamin $D_3$ derivative on preparative silica gel tlc, using Skellysolve B:ethyl acetate, 3:1) or as the product from Example 2, and 6.0 mg of tosylchloride. After 18 hr. at 3° the reaction is quenched with saturated NaCl solution, extracted with ether, and the ether extracts washed repeatedly with a saturated $NaHCO_3$ solution. After drying over $MgSO_4$, and removal of the solvent in vacuo the crude 1α-acetoxyvitamin $D_3$ 3-tosylate is taken up in 3.0 ml of anhydrous MeOH buffered with 12.0 mg of $NaHCO_3$. The reaction mixture is heated to 55° overnight, quenched with saturated solution of NaCl, extracted with ether and the solvent is removed in vacuo. The crude product is subjected to preparative tlc (5×20 cm, 250 μm silica gel, Skellysolve B:ethyl acetate, 3:1) to yield 2.2 mg of 1α-hydroxycyclovitamin $D_3$ (3a) which is identical in all respects to the product obtained in Example 1.

EXAMPLE 28

$MnO_2$ oxidation of 1α-hydroxycyclovitamin $D_3$ (3a) to 1-oxo-cyclovitamin $D_3$ (7a)

To 1.0 ml of dry $CH_2Cl_2$ is added 3.0 mg of 1α-hydroxycyclovitamin $D_3$ (3a) and 35 mg of finely divided $MnO_2$. [See for example, Paaren et al. J. Chem. Soc., Chem. Comm. 890 (1977)]. After 2.0 hr. the reaction mixture is filtered through celite to yield, after preparative tlc (5×20 cm, 250 μm, silica gel, Skellysolve B:ethyl acetate), 2.6 mg of 1-oxo-cyclovitamin $D_3$ (7a) identical in all respects to the product described in Example 1.

Having thus described the invention what is claimed is:

1. A method for preparing 1α-hydroxylated vitamin D compounds having the general formulae

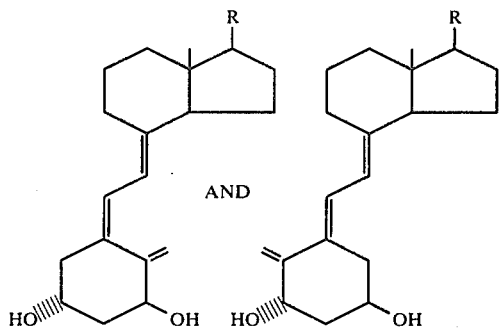

wherein R is selected from the group consisting of substituted or unsubstituted, or saturated or unsaturated, or unsaturated and substituted cholesterol side chain groups, or where R may have the structure of the side chain of cholenic acid, or of homocholenic acid, or of 27-nor-25-ketocholesterol, or of 24-ketocholesterol, which comprises subjecting compounds having the general formula

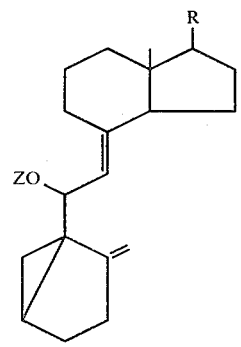

wherein R is defined as above and Z is selected from the group consisting of hydrogen, lower alkyl, lower acyl and aromatic acyl to allylic oxidation with selenium dioxide, recovering the corresponding 1α-hydroxy compound, acylating said 1α-hydroxy compound to form the 1α-O-acyl derivative, subjecting said derivative to acid catalyzed solvolysis, whereby the 5,6-cis and 5,6-trans-1α-O-acyl vitamin D compounds are produced in admixture, and removing the acyl groups from said compounds by hydrolysis or hydride reduction.

2. The method of claim 1 wherein the allylic oxidation is carried out in the presence of a hydroperoxide.

3. The method of claim 2 wherein the peroxide is hydrogen peroxide.

4. The method of claim 2 wherein the peroxide is an alkyl hydroperoxide.

5. The method of claim 1 wherein the solvolysis of the 1α-O-acyl derivative is accomplished in the presence of p-toluene sulfonic acid.

6. The method of claim 1 wherein the solvolysis of the 1α-O-acyl derivative is carried out in a solvent comprising an organic carboxylic acid, whereby the 5,6-cis and 5,6-trans-1α,3β-di-O-acylvitamin D compounds are obtained.

7. The method of claim 6 wherein the organic carboxylic acid is glacial acetic acid or formic acid.

8. The method of claim 6 wherein the 5,6-cis and 5,6-trans-1α,3β-di-O-acyl solvolysis products are separated prior to removal of the acyl groups.

9. The method of claim 1 wherein the solvolysis of the 1α-O-acyl derivative is accomplished in the presence of a crown ether compound.

10. The method of claims 1 or 5 wherein the 5,6-cis and 5,6-trans 1α-O-acyl solvolysis products are separated prior to removal of the acyl groups.

11. The method of claims 6 or 8 wherein one of the acyl groups in the 1α,3β-di-O-acyl solvolysis products is removed by selective hydrolysis prior to separation of the 5,6-cis and 5,6-trans isomers.

12. The method of claim 1 wherein Z is lower alkyl.

13. The method of claim 1 where, in the cyclovitamin starting material, R has the formula

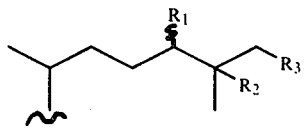

wherein each of $R_1$, $R_2$, and $R_3$ are selected from the group consisting of hydrogen, hydroxyl, lower alkyl, O-lower alkyl, O-lower acyl, O-aromatic acyl, and fluorine.

14. The method of claim 13 wherein $R_1$ and $R_3$ are hydrogen and $R_2$ is hydroxyl.

15. The method of claim 13 wherein $R_1$, $R_2$, and $R_3$ are hydrogen.

16. The method of claim 13 wherein $R_1$ is hydroxyl and $R_2$ and $R_3$ are hydrogen.

17. The method of claim 13 wherein $R_1$ and $R_2$ are hydroxyl and $R_3$ is hydrogen.

18. The method of claim 1 where, in the cyclovitamin starting material, R has the formula

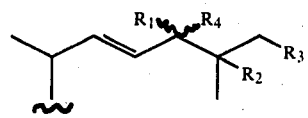

wherein each of $R_1$, $R_2$, and $R_3$ are selected from the group consisting of hydrogen, hydroxyl, lower alkyl, O-lower alkyl, O-lower acyl, O-aromatic acyl, and fluorine, and $R_4$ is selected from the group consisting of hydrogen and lower alkyl.

19. The method of claim 18 wherein $R_1$, $R_2$, and $R_3$ are hydrogen and $R_4$ is methyl, having the stereochemistry of the ergosterol side chain.

20. The method of claim 18 wherein $R_1$ and $R_3$ are hydrogen, $R_2$ is hydroxyl and $R_4$ is methyl, with the stereochemistry of the ergosterol side chain.

21. Compounds having the formula

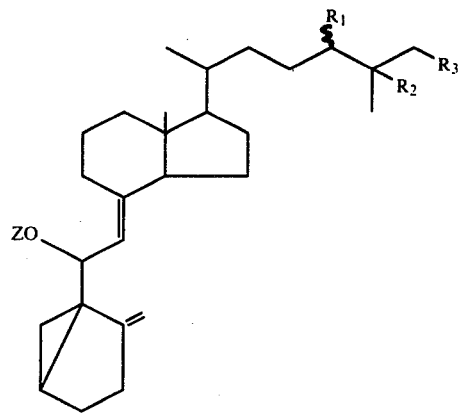

wherein Z is selected from the group consisting of hydrogen, lower alkyl, lower acyl, and aromatic acyl, and, each of $R_1$, $R_2$, and $R_3$ are selected from the group consisting of hydrogen, hydroxyl, lower alkyl, O-lower alkyl, O-lower acyl, benzoate and fluorine and, except that when Z is hydrogen or methyl and both $R_1$ and $R_3$ are hydrogen, $R_2$ cannot be hydrogen.

22. A compound according to claim 21 wherein $R_1$ and $R_3$ are hydrogen and $R_2$ is hydroxyl.

23. Compounds according to claims 21 or 22 wherein Z is methyl.

24. Compounds having the formula

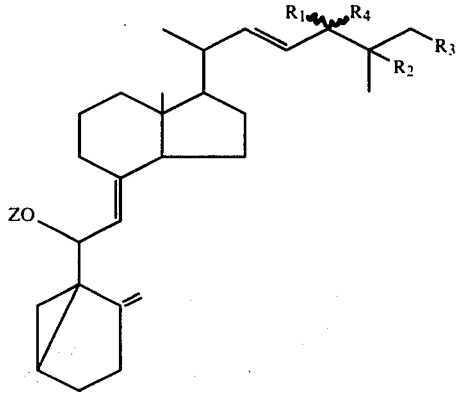

wherein Z is selected from the group consisting of hydrogen, lower alkyl, lower acyl, and aromatic acyl, each of $R_1$, $R_2$, and $R_3$ are selected from the group consisting of hydrogen, hydroxyl, lower alkyl, O-lower alkyl, O-lower acyl, benzoate, and fluorine and $R_4$ is selected from the group consisting of hydrogen and lower alkyl.

25. A compound according to claim 24 wherein $R_1$, $R_2$, and $R_3$ are hydrogen and $R_4$ is methyl, having the stereochemistry of the ergosterol side chain.

26. A compound according to claim 24 wherein $R_1$ and $R_3$ are hydrogen, $R_2$ is hydroxyl and $R_4$ is methyl, having the stereochemistry of the ergosterol side chain.

27. Compounds according to claims 24, 25 or 26 wherein Z is methyl.

28. Compounds having the formula

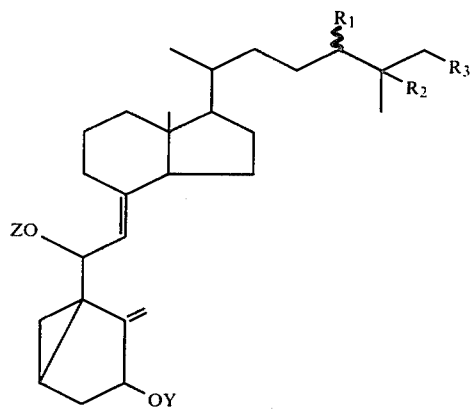

wherein Z is selected from the group consisting of hydrogen, lower alkyl, lower acyl, and aromatic acyl, each of $R_1$, $R_2$ and $R_3$ are selected from the group consisting of hydrogen, hydroxyl, lower alkyl, O-lower alkyl, O-lower acyl, benzoate, and fluorine, and Y is selected from the group consisting of hydrogen, lower acyl and aromatic acyl.

29. Compounds having the formula as shown in claim 28 wherein Z is methyl and Y is hydrogen.

30. Compounds having the formula as shown in claim 28 wherein Z is methyl and Y is lower acyl.

31. Compounds having the formula

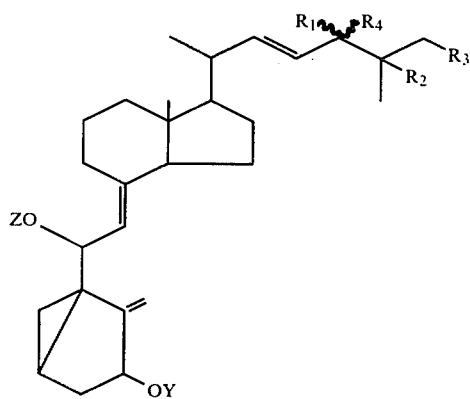

wherein Z is selected from the group consisting of lower alkyl, lower acyl, aromatic acyl or hydrogen, each of $R_1$, $R_2$, and $R_3$ are selected from the group consisting of hydrogen, hydroxyl, lower alkyl, O-lower alkyl, O-lower acyl, benzoate and fluorine, $R_4$ is se- lected from the group consisting of hydrogen and lower alkyl, and Y is hydrogen, lower acyl or aromatic acyl.

32. Compounds having the formula of claim 31 wherein Z is methyl and Y is hydrogen.

33. Compounds having the formula of claim 31, wherein Z is methyl and Y is lower acyl.

34. Compounds having the formula

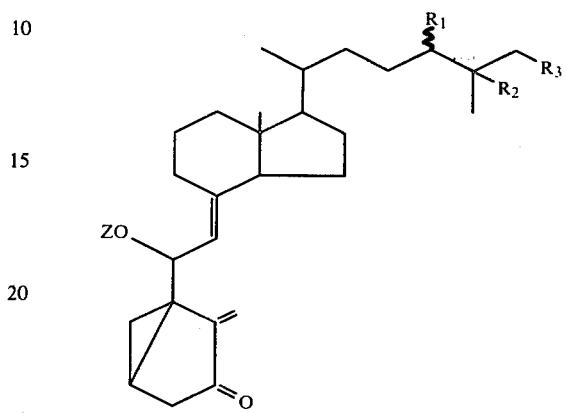

wherein Z is hydrogen or lower alkyl, each of $R_1$, $R_2$, and $R_3$ are selected from the group consisting of hydrogen, hydroxyl, lower alkyl, O-lower alkyl, O-lower acyl, benzoate and fluorine.

35. Compounds having the formula

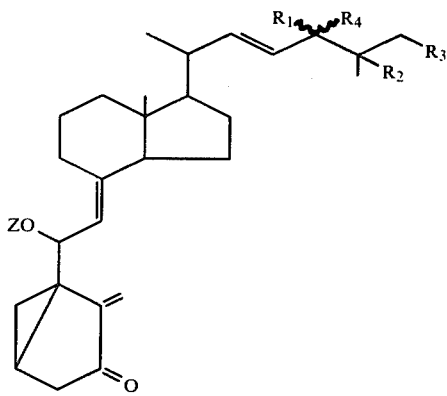

wherein Z is hydrogen or lower alkyl, each of $R_1$, $R_2$, and $R_3$ are selected from the group consisting of hydrogen, hydroxyl, lower alkyl, O-lower alkyl, O-lower acyl, benzoate, and fluorine, and where $R_4$ is hydrogen or lower alkyl.

36. 1α-hydroxy-6-alkznoxy-3,5-cyclovitamin $D_3$.

37. 1α-O-acyl derivatives of the compounds of claim 36.

38. 1α,25-dihydroxy-6-alkanoxy-3,5-cyclovitamin $D_3$.

39. 1α-O-acyl derivatives of the compounds of claim 38.

40. 1α,25-O-diacyl derivatives of the compounds of claim 38.

41. 1α-hydroxy-6-methoxy-3,5-cyclovitamin $D_3$.

42. 1α-acetoxy-6-methoxy-3,5-cyclovitamin $D_3$.

43. 1α,25-dihydroxy-6-methoxy-3,5-cyclovitamin $D_3$.

44. 1α-acetoxy-25-hydroxy-6-methoxy-3,5-cyclovitamin $D_3$.

45. 1α,25-diacetoxy-6-methoxy-3,5-cyclovitamin $D_3$.

46. 1α,25-dihydroxy-6-alkanoxy-3,5-cyclovitamin D$_3$.

47. 1α-O-acyl derivatives of the compounds of claim 46.

48. 1α,25-O-diacyl derivatives of the compounds of claim 46.

49. 1α-hydroxy-6-alkanoxy-3,5-cyclovitamin D$_2$.

50. 1α-O-acyl derivatives of the compounds of claim 49.

51. 1α-hydroxy-6-methoxy-3,5-cyclovitamin D$_2$.

52. 1α-acetoxy-6-methoxy-3,5-cyclovitamin D$_2$.

53. 1α,25-dihydroxy-6-methoxy-3,5-cyclovitamin D$_2$.

54. 1α-acetoxy-25-hydroxy-6-methoxy-3,5-cyclovitamin D$_2$.

55. 1α,25-diacetoxy-6-methoxy-3,5-cyclovitamin D$_2$.

56. 1α,24,25-trihydroxy-6-alkanoxy-3,5-cyclovitamin D$_3$.

57. The 1α-O-acyl derivative of the compounds of claim 56.

58. The 1α,24,25-tri-O-acyl derivative of the compounds of claim 56.

59. The compound of claim 56 wherein the alkanoxy is methoxy.

60. The 1α,24,25-tri-O-acyl derivative of the compound of claim 59.

61. 1-oxo-6-alkanoxy-3,5-cyclovitamin D$_3$.

62. 1-oxo-25-hydroxy-6-alkanoxy-3,5-cyclovitamin D$_3$.

63. 1-oxo-24,25-dihydroxy-6-alkanoxy-3,5-cyclovitamin D$_3$.

64. 1-oxo-6-alkanoxy-3,5-cyclovitamin D$_2$.

65. 1-oxo-25-hydroxy-6-alkanoxy-3,5-cyclovitamin D$_2$.

* * * * *

UNITED STATES PATENT OFFICE
CERTIFICATE OF CORRECTION

Patent No. 4,195,027　　　　　　　　Dated March 25, 1980

Inventor(s) Hector F. DeLuca et al

It is certified that error appears in the above-identified patent and that said Letters Patent are hereby corrected as shown below:

Column 4, line 57, "(5-10%" should be --(5-10%)--

Column 7, line 33, "(75°-100° 1 C.)." should be --(75°-100° C.).--

Column 12, line 23, "designated" should be --designating--

Column 20, line 58, "reoved" should be --removed--

Column 29, line 2, "$D_3$" should be --$D_2$--

*Signed and Sealed this*

*Eighth* Day of *July 1980*

[SEAL]

*Attest:*

SIDNEY A. DIAMOND

*Attesting Officer*　　*Commissioner of Patents and Trademarks*